United States Patent [19]

Dedinas et al.

[11] 4,081,278

[45] Mar. 28, 1978

[54] HEAT SENSITIVE DYE LAYERS COMPRISING A BENZOPINACOL

[75] Inventors: Jonas Dedinas; George Leland Fletcher, Jr., both of Pittsford, N.Y.

[73] Assignee: Eastman Kodak Company, Rochester, N.Y.

[21] Appl. No.: 799,797

[22] Filed: May 23, 1977

[51] Int. Cl.² ............................ G03C 1/02; G03C 5/24
[52] U.S. Cl. ................................ 96/48 HD; 96/114.1; 96/67; 96/53
[58] Field of Search .................. 96/114.1, 53, 48 HD, 96/67

[56] References Cited

U.S. PATENT DOCUMENTS

| | | | |
|---|---|---|---|
| 1,517,049 | 11/1924 | Christensen | 96/53 |
| 3,734,733 | 5/1973 | Poot et al. | 96/48 HD |
| 3,788,849 | 1/1974 | Taguchi et al. | 96/48 HD |
| 3,801,321 | 4/1974 | Evans et al. | 96/114.1 X |

*Primary Examiner*—Edward C. Kimlin
*Assistant Examiner*—Alfonso T. Suro Pico
*Attorney, Agent, or Firm*—Richard E. Knapp

[57] ABSTRACT

A heat bleachable layer comprising a benzopinacol and a reducible dye or dye precursor is useful in an imaging element. The heat bleachable layer can be, for instance, an antihalation layer of a photographic element, such as a photothermographic element.

28 Claims, No Drawings

HEAT SENSITIVE DYE LAYERS COMPRISING A BENZOPINACOL

BACKGROUND OF THE INVENTION

1. Field of the Invention

The present invention relates to an element having at least one layer that changes its electromagnetic absorption characteristics on the application of heat. This layer is useful, for example, as a filter layer or an antihalation layer in a photographic element, such as a photothermographic element. The element is also useful as a thermographic recording element. The element of the present invention has at least one layer containing a benzopinacol and a bleachable dye or dye precursor.

2. Discussion of the State of the Art

A large number of photographic elements are known which can be processed by immersion in various processing solutions. It is also known to provide various filter layers including filter overcoat layers, filter interlayers and antihalation layers, to improve photographic reproduction. The filtering capability of these layers is generally destroyed during the processing of these elements by one of the processing solutions so that the processed element is entirely transparent in the visible region.

Imaging elements are also known which can be processed, after imagewise exposure, simply by heating the element. These elements include known heat developable photographic elements, also known as photothermographic elements. Like conventional elements, it is desirable to provide heat processable elements with various filter layers. In most cases, these filter layers must be rendered substantially transparent by the heat processing. Typical heat developable photographic elements are described, for example, in U.S. Pat. No. 3,220,846 of Sagura and Tinker, issued Nov. 30, 1965; U.S. Pat. No. 3,301,678 of Humphlett, Johnson and Haist, issued Jan. 31, 1967; British Pat. No. 1,161,777 published Aug. 20, 1969; U.S. Pat. No. 3,392,020 of Yutzy and Yackel, issued July 9, 1968; British Pat. No. 930,572 published July 3, 1963; U.S. Pat. No. 3,152,904 of Sorenson et al, issued Oct. 13, 1964; U.S. Pat. No. 3,457,075 of Morgan et al, issued July 22, 1969; and U.S. Pat. No. 3,801,321 of Evans and McLaen, issued Apr. 2, 1974.

The antihalation layer of a photographic element prevents light that has passed through the radiation sensitive layer from reflecting off of the support and back into the light sensitive layer. If not prevented, this reflected light could reduce the sharpness of the image. Antihalation layers, and other filter layers, have been suggested for use with heat developable photographic elements. One such antihalation layer is described in U.S. Pat. No. 3,745,009 to Jenkins, Heseltine and Mee. This patent describes a class of dyes which change from color to colorless on exposure to heat or light. No separate activating component is used. These dyes provide antihalation protection; however, these dyes generally require higher temperatures than desired before they decompose. In U.S. Pat. No. 3,769,019 of Wiese et al an antihalation layer is described wherein the acid component of a dye is neutralized by a heat generated base. In another embodiment described in this patent, decoloration of the dye is accomplished by removal of an acid portion by heat. Unfortunately, decoloration of the dye is not always as permanent as desired. U.S. Pat. No. 3,821,001 of Weber describes another antihalation layer containing an alkali bleachable vanadium complex of 8-hydroxyquinoline and a heat labile alkali precursor. In many cases higher temperatures than desired are required to provide the degree of decoloration desired. Photobleachable antihalation dyes are also known, as described, for example, in U.S. Pat. No. 3,984,248 of Sturmer, issued Oct. 5, 1976. It is often desired that the antihalation layer not be photosensitive.

A continuing need has existed for improved antihalation layers and other filter layers, that (a) can be decolorized simply by the application of heat but which are stable during storage at ambient conditions and (b) provide improved permanence in maintaining the desired degree of transparency of the layers after processing.

Typically, layers which can be used as antihalation layers, or other filter layers in a photothermographic element, can also be useful alone on a support to provide a thermographic element. In these embodiments, any color change can be useful to form an image. For example, a substantially colorless dye precursor can be imagewise thermally bleached to form a positive colored image. Of course, a colored dye can be imagewise thermally bleached to a colorless state thereby forming a negative image. A variety of thermographic materials are known that use this concept. For example, U.S. Pat. No. 3,852,093 of O'Leary describes a thermographic element having a layer containing an imine dye and a mild reducing agent. Brief imagewise heating of the element causes migration of the reactants which results in decoloration in the imagewise heated area. All of these thermographic elements are useful for making reflex copies, writing with heated styluses and laser writing. Examples of these embodiments are described in U.S. Pat. No. 3,745,009 of Jenkins et al.

All of the heat bleachable elements described have at least one of the disadvantages: (1) frequently high temperature is required to bleach the dye, (2) in some cases even when the dye is bleached it has a tendency to recombine forming undesired stain or discoloration on prolonged post process keeping, and (3) choice of suitable dyes is greatly limited.

SUMMARY OF THE INVENTION

It has been found according to the invention that a benzopinacol incorporated in an imaging element and heated forms ketyl radicals which can reduce a reducible dye or a reducible dye precursor also in the element thereby bleaching the dye. The described advantages are accordingly provided by an imaging element comprising a support having thereon a neutral or acidic heat bleachable layer comprising (i) a binder, (ii) a benzopinacol which forms ketyl radicals on heating to a temperature above 100° C and (iii) a reducible dye or a reducible dye precursor. The benzopinacol, which is ordinarily unstable in solution, can be incorporated in a binder in a neutral or acidic layer and be stable for long periods. While some of the elements containing benzopinacols described herein require somewhat higher temperatures or longer times to form ketyl radicals, preferred elements according to the invention require heating to a temperature of about 160° for less than 10 seconds. The heat generated ketyl radicals react with a described dye in a substantially irreversible reaction to provide a desired degree of decoloration permanence.

The heat bleachable benzopinacol-dye layers described herein are useful in a variety of ways to improve photographic reproduction.

Detailed Description of the Invention

A wide variety of benzopinacols can be used according to the present invention. The useful benzopinacols form ketyl radicals, it is believed by a dissociation reaction, on being heated to a temperature above 100° C.

Whether a particular benzopinacol dissociates to ketyl radicals above 100° C can be determined by spectrophotometric analysis. The benzopinacol in question is coated with the desired binder under neutral or acidic conditions, but without a dye, on a transparent support. In the absence of a dye, the ketyl radicals, if formed, will disproportionate to form a benzophenone and a benzhydrol. The benzopinacol will display no absorption in the UV region, 300–400 nm, the generated benzophenone will display an absorption peak at about 345 nm. If the benzophenone peak does not form at a temperature of up to about 160° C, e.g., within the range of about 100° C to about 160° C, after being heated for a period of less than 1 hour the benzopinacol is considered not to be useful in the present invention. A similar test in the presence of an azo dye is used to determine preferred benzopinacols which dissociate and react with the azo dye at 160° C in less than 10 seconds. Useful benzopinacols can be described by, but are not limited to, compounds described by the following formulae:

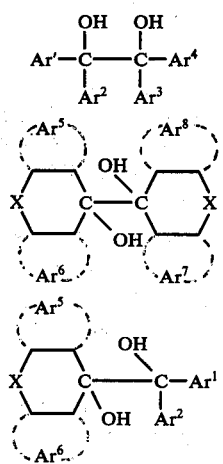

wherein X is a covalent bond, oxygen, sulphur, —CH$_2$—, —CH$_2$CH$_2$—, —CH—Ar and the like, and wherein Ar$^1$ through Ar$^4$ are independently selected and represent substituted or unsubstituted aromatic groups; and Ar$^5$ through Ar$^8$ are independently selected and represent the atoms necessary to complete substituted or unsubstituted aromatic groups. The substituents on the aromatic groups can be of any of a wide variety including, but not limited to, alkyl, cyano, halogen, alkyl or aryl sulfonyl, alkoxy, such as methoxy and ethoxy, nitroso, nitro substituted amino and the like.

A preferred class of benzopinacols includes those represented by the formula:

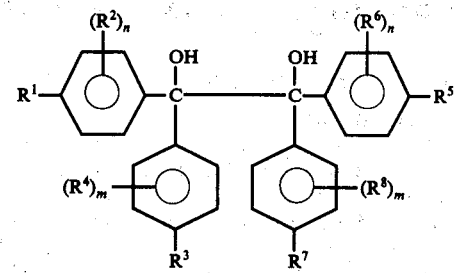

wherein each R$^1$ and R$^5$ is independently selected from halogen atoms, such as fluorine, bromine and chlorine atoms, alkyl of about 1 to 10 carbon atoms including halo substituted alkyl such as chloromethyl, alkoxy having about 1 to 10 carbon atoms, such as methoxy and ethoxy, phenoxy having about 6 to 12 carbon atoms and hydroxy; R$^3$ and R$^7$ are independently selected from hydrogen atoms or any of the groups specified for R$^1$ and R$^5$; each R$^2$, R$^4$, R$^6$, and R$^8$ is independently selected from halogen atoms, such as fluorine bromine and chlorine, preferably fluorine, and from trifluoromethyl with the proviso that both ortho positions on each of the four phenyl groups can be substituted only when both substituents are fluorine; each n independently is an integer of from 1 to 4; and each m independently is an integer of from 0 to 4. These substituted benzopinacols generally require somewhat lower activation temperatures while at the same time remaining stable for longer periods of time in imaging elements.

Combinations of different benzopinacols can also be useful in the described benzopinacol-dye layers.

A highly preferred class of benzopinacols are those described in copending application entitled "Substituted Benzopinacols and Their Preparation", Ser. No. 799,798 to Dedinas filed herewith and incorporated herein by reference. These benzopinacols produce ketyl radicals which are more reactive than ketyl radicals produced from other benzopinacols while retaining the other advantages of ease of processing and long shelf life. These preferred benzopinacols can be represented by the formula:

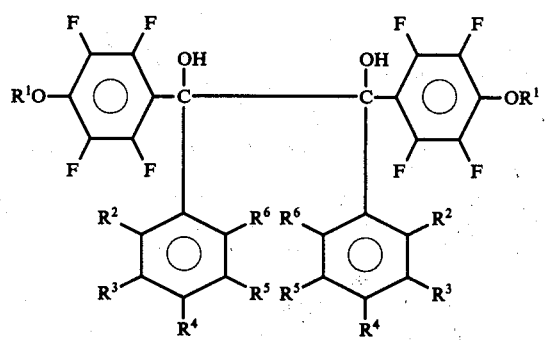

wherein

R$^1$ is hydrogen; alkyl including cycloalkyl, such as alkyl containing 1 to 16 carbon atoms, for example, methyl, ethyl and propyl, including substituted alkyl; or aryl, including substituted aryl, such as methoxyphenyl, methylphenyl and the like;

R$^2$ and R$^6$ independently are selected from the group consisting of hydrogen, halogen and trifluoromethyl;

$R^3$ and $R^5$ independently are selected from the group consisting of hydrogen, halogen and alkyl including cycloalkyl, such as alkyl containing 1 to 16 carbon atoms, for example, methyl, ethyl and propyl, including substituted alkyl or when taken together with $R^4$ represent a tetramethylene group; and $R^4$ is selected from the group consisting of hydrogen; halogen; alkyl, such as alkyl containing 1 to 16 carbon atoms, for example, methyl, ethyl and propyl, including cycloalkyl and substituted alkyl; alkoxy; and phenoxy, including substituted alkoxy and phenoxy such as methoxyphenoxy, methylphenoxy and the like;

with the proviso that when both of the ortho positions of the phenyl groups at which $R^2$ and $R^6$ are attached are substituted, the substituent is fluorine.

Useful binders for the imaging layer and the benzopinacol containing layer vary widely. Since the elements of the present invention need not be processed in aqueous solutions, useful binding agents need not be water permeable, however, they must be compatible with the benzopinacol and dye used. By compatible it is meant that the binder must not adversely affect the benzopinacol or the dye and not adversely affect the desired imaging properties of the imaging element. Illustrative binders include, for instance, cellulose ester derivatives such as alkyl esters or carboxylated cellulose, polyacetals such as poly(vinyl butyral) and poly(vinyl formal), poly(vinyl alcohol), various vinyl polymers such as poly(vinylidene halides), polymers of α, β-ethylenically unsaturated carboxylic acids such as poly(methyl methacrylate) and the like. The selected binder must be able to withstand the processing temperatures employed without adversely affecting the desired properties of the layer. Combinations of various binders can also be useful. The preferred binders are polysulfonamide binders.

While the benzopinacols may be mixed with a wide variety of binders to form the bleachable layers according to the invention, particularly preferred binders are the polysulfonamide binders described in "Polysulfonamide Vesicular Binders", U.S. Ser. No. 645,178, filed Dec. 29, 1975 to G. L. Fletcher et al which is hereby incorporated by reference in *Research Disclosure*, March 1975, Item No. 13107, published by Industrial Opportunities Ltd., Homewell, Havant Hampshire, P09 1EF, UK. Benzopinacols in polysulfonamide binders exhibit improved stability during long-term storage and improved image-forming properties. The sulfonamide polymer has in the backbone or pendent therefrom, the moiety $-SO_2-N<$ and further has the property that the wavelength of maximum absorption is no greater than about 350 nm in the spectral range from 200 to 750 nm.

While it is not completely understood why the polysulfonamide binders improve the keeping characteristics of layers containing benzopinacols, the following hypothesis has been suggested. The instability of the benzopinacol in the coating may be due to the premature formation of ketyl radicals. The high diffusional activation energy of the polysulfonamide binders may inhibit the diffusion of the ketyl radicals away from the decomposing benzopinacol and thus may stabilize the compound by promoting recombination of the radicals to reform the original compound. Alternatively, it may be that the acid character of the polysulfonamide binder inhibits the decomposition of the benzopinacol. Whatever the mechanism, polysulfonamide binders provide benzopinacol layers with improved keeping characteristics.

It has been found that a variety of sulfonamide polymers having the group $-SO_2-N<$ as a portion of the polymer backbone or as a pendent moiety is useful, provided that the wavelength of maximum absorption of the binder is no greater than about 350 nm in a spectral range between 200 and 750 nm. Particularly, useful classes of such polymers include polymers containing toluene-2,4-disulfonamide units and those containing N-(vinylphenyl) sulfonamide units. These binders can be homopolymers, copolymers, or physical mixtures of the polysulfonamide polymers. Whether the polymer is an addition polymer or a condensation polymer, a minimum portion of the polymer should be recurring sulfonamide groups such as $-SO_2-N<$ groups, so that the weight percent of sulphur is at least about 4%.

The concentration of binder can also vary over a wide range. Typically, the weight of any reactive components, including the benzopinacol and dye, to the weight of the binder should not be above about 50%. Preferably the coating contains between 50% and 99% binder and it is preferred that the coating contain 80% to 95% binder.

Any dye can be used according to the invention which is known to exhibit a change in its electromagnetic radiation-absorption characteristics upon reduction and which can react with the described ketyl radicals. For antihalation layers for example, it is desirable that the heat bleachable layer have substantially uniform absorption in the spectral region where the image-forming composition is sensitive. The antihalation layer should be reduced so that at least about 90% of the layer is changed from colored to colorless or it has substantially no density.

In thermographic applications a substantially colorless dye can be reduced according to the invention to a colored form to produce a positive image in those areas where the element is heated. In other thermographic applications, a change in color upon reduction of the dye may be adequate.

A variety of dyes are known which are bleached or converted to a colored form upon reduction. Dyes of this type have long been used, for example, in silver-dye-bleach processes. These dyes can be useful in the practice of this invention. Dyes of this type include those described in Christensen, U.S. Pat. No. 1,517,049. Other reducible dyes of this type include those described by J. S. Friedman in History of Color Photography, Chapter 24, published 1944. Other bleachable dyes include, for example, cyanine dyes, diphenyl methine dyes, formazan dyes, aminotriarylmethine and thiocyanine dyes. Triazine dyes and indigo dyes provide less than optimum results. This is applicable to most xanthene dyes also. It is necessary that the dyes be sufficiently reducible to react with the ketyl radicals formed from the benzopinacol upon heating.

While several classes of reducible dyes and reducible dye precursors are useful according to the invention, a preferred class of reducible dyes are the azo dyes because they are very reactive toward the described ketyl radicals, and because the reactions are irreversible. Any azo dyes are useful, such as azo dyes having single or multiple azo groups including those represented by the formulas:

Ar—N=N—Ar and

Ar—N=N—Ar—N=N—Ar—N=N—Ar wherein Ar represents an aromatic group which can contain any of the substituents well known in the azo dye art. These substituents include alkyl, aryl, cyano, halogen, halogen substituted alkyl and aryl such as trifluoromethyl, alkyl or aryl sulfonyl such as ethyl sulfonyl and methyl sulfonyl, alkoxy such as methoxy and ethoxy, nitroso, nitro, substituted amino such as diethylamino and dimethylamino, and the like. Included in this class of dyes are azo dyes such as monoazo and diazo dyes, such as those having amino, pyrazolone, hydroxy, alkoxy and other substituents; diazo dyes having stilbene and triphenyl methane linkages. Exemplary useful azo dyes are described in U.S. Pat. Nos. 1,829,673; 1,985,344; 2,004,625; 2,028,279; 2,055,407; 2,074,259; 2,075,191; 2,080,041; 2,100,594; 2,166,049; 2,172,307; 2,183,395; 2,217,899; 2,231,685; 2,271,176; 2,281,149; 2,286,838; 2,294,892; 2,294,893; 2,331,755; 2,304,884; 2,350,736; 2,368,647; 2,418,624; 2,420,630; 2,420,631; 2,564,238; 2,612,448; 2,629,658; 2,681,856; 2,694,636; 2,899,305; 3,002,964; 3,157,508; and 3,167,537 which are incorporated by reference.

The benzopinacol dye layers of the elements of the present invention should be neutral or acidic. In order to provide a neutral layer or the desired degree of acidity, an acid, typically an organic acid, inorganic or Lewis type acid, may be added to the coating composition prior to coating. Useful acids include toluene sulfonic acid, acetic acid, hydrochloric acid, aluminum chloride and the like. In some embodiments this may not be necessary since the binder itself may provide the necessary acidity for the layer. Since many of the layers of the present invention, such as layers using the polysulfonamide binders, are not coated from aqueous solutions, it is sometimes difficult to determine whether or not the layer is acidic. The following simple test, however, provides an easy method for making such a determination.

It is known that many dyes change their spectral absorption characteristics when they are protonated, such as when they are in an acidic environment. Such an indicator dye can be added to a coating composition with unknown acidity. The same indicator dye is added to a portion of the coating composition to which has been added a significant amount of a base. The same indicator dye is added to a third portion of the coating composition to which has been added a significant amount of acid. The three coating compositions are then coated on the support under the desired conditions of coating. Spectral absorption curves are then obtained for the three samples and the unknown sample is compared to the "acid" and "basic" samples. The unknown sample then can be determined to be acidic or basic by comparison of the absorption spectrum of the indicator dye in the unknown sample with the absorption spectra of the indicator dye in the presence of acid and base. A very sensitive indicator is the following azo dye (indicator dye A) when it is used in the coating in the presence of decafluorobenzopinacol.

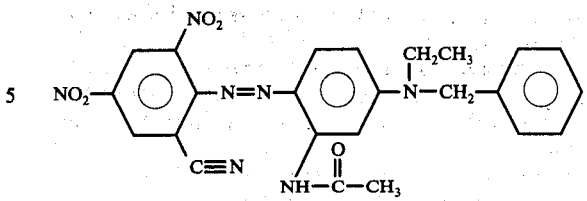

N-Benzyl-N-ethyl-3-acetamido-4-(2-cyano-4,6-dinitrophenylazo)aniline

The following experiment shows the absorption spectrum of the indicator dye A under neutral conditions and as a function of concentration of added acid and base.

A coating is made using a solution containing the indicator dye A, a polymer, and decafluorobenzopinacol. The solvent used was 2-methoxyethanol. Using this composition, basic conditions of a coating are defined when the indicator dye has no significant absorption in the visible region. There is no $\lambda_{max}$ at 620 nm and no $\lambda_{max}$ at 490 nm. Neutral conditions are defined when there is $\lambda_{max}$ at 620 nm but no $\lambda_{max}$ at 490 nm. Acidic conditions are defined when there is $\lambda_{max}$ at 490 nm but no $\lambda_{max}$ at 620 nm. To illustrate this, elements are made with the above coating composition varying the amount of acid (toluene sulfonic acid) or base (triethanolamine) added to the coating composition. These test coatings contain 20 mg of indicator dye A and 550 mg of decafluorobenzopinacol in 10 ml of 2-methoxyethanol. This solution is added to a 10 ml solution of 20% polysulfonamide in 2-methoxyethanol. Two milliliters of this solution is then poured into vials containing various amounts of acid or base dissolved in 0.1 ml of acetone. After mixing, the solutions are coated on poly(ethylene terephthalate) and dried at 120° F (47° C) for 10 minutes. The results are indicated below. E is the extinction coefficient at the indicated wavelength.

| Acid or Base, mg/2 ml. | max (1) | $E_{620}$ | max (2) | $E_{490}$ |
|---|---|---|---|---|
| 0.0 | 620 nm | .98×10⁴ | none | — |
| 1 mg base | 620 nm | .34×10⁴ | none | — |
| 3 mg base | none | .24×10⁴ | none | — |
| 7 mg base | none | .067×10⁴ | none | — |
| 12 mg base | none | .013×10⁴ | none | — |
| 1 mg acid | 620 nm | .50×10⁴ | 490 | .27×10⁴ |
| 2 mg acid | none | .052×10⁴ | 490 | .63×10⁴ |
| 3.5 mg acid | none | .013×10⁴ | 490 | .67×10⁴ |

Using this calibration for the indicator dye A, the acidity of an unknown coating can be determined. The unknown coating is dissolved from the support, the indicator dye A, decafluorobenzopinacol and optionally additional polymeric binder (polysulfonamide) is added and the resulting solution is then recoated. Spectrophotometric analysis can then be used to determine qualitatively whether the original coating was neutral, basic or acidic.

The coverages and proportions of the various components which form the benzopinacol-dye layers of the present invention can vary over extremely wide ranges depending upon the application. For example, in some thermographic applications, the dye need only be present to provide an optical density of at least about 0.05. To provide image discrimination, the benzopinacol need only be present in an amount sufficient to reduce the density of the dye by about 10% when the element is heated above 100° C. For antihalation layers on the other hand, it is desirable that the dye be present in an amount sufficient to provide an optical density of about 0.3 to 0.8 and that the benzopinacol be present in at least a stoichiometric amount. When azo dyes are used, for example, the stoichiometric amount is 2 moles of benzopinacol to 1 mole of azo dye. Typically, an excess of the benzopinacol insures the complete reduction of the azo dyes in embodiments where that is desirable. The upper molar ratio of benzopinacol to azo dye is determined by economic considerations and can be as high as 30:1. The preferred range is between about 1:1 to 4:1 with the optimum ratio for complete reduction being about 2.4:1.

For a thermographic embodiment of the invention the benzopinacol-dye layer is simply coated on a suitable support. In photothermographic embodiments the layers may be coated in contact with the light-sensitive layer or the benzopinacol-dye components may be included in the light-sensitive layers. The heat bleachable layers can be used as light screening layers, such as a layer coated directly on top of the light-sensitive layers or between two light-sensitive layers or between the support and a light sensitive layer or on the back of a support as an antihalation layer.

The heat bleachable layers and other layers of an element of the present invention can be coated by any of a wide variety of methods known in the photographic art, such as doctor blade coating, hopper coating, dipping, spraying and the like.

The dyes which are useful in the present invention can be mordanted to prevent their wandering into undesirable locations in the imaging element. Any of a wide variety of mordants which are known in the photographic art can be useful.

The imaging elements described herein can comprise a wide variety of supports. In some embodiments, such as thermographic embodiments, the support need not be transparent and can be such materials as paper, particularly acetylated or coated with baryta and/or an α-olefin polymer, metal, glass or the like. In embodiments where the support should be transparent, common photographic supports can be useful, such as cellulose acetate film, poly(vinylacetal) film, polystyrene film, poly(ethylene terephthalate) film, polycarbonate film, polyester film or related films or resinous materials.

The benzopinacol-dye layers described herein can be coated in a variety of photographic elements. The layer may, for example, be coated on a conventional solution processable element. Heating of the element, such as in the dryer section of a wet processing machine, can cause the layer to change color.

The benzopinacol-dye layers can be useful in elements having a variety of photosensitive layers. Examples of suitable photosensitive layers are conventional photosensitive silver halide layers, diazo layers, photopolymerizable layers, vesicular imaging layers and the like. The layers that are particularly useful are layers for heat developable photographic elements, i.e. photothermographic elements. An embodiment of the invention is a photothermographic element comprising a support having thereon (1) a heat bleachable antihalation layer, as described herein, and (2) a layer comprising, (a) a photographic silver salt, typically photographic silver halide, (b) a photographic silver salt developing agent, (c) a binder and (d) a heat activatable activator for the developing agent. The photothermographic element can also comprise (e) a heat activatable stabilizer for the silver salt. In many photothermographic elements, (d) and (e) are a single activator-stabilizer compound, an example being an α-sulfonylacetate activator stabilizer. Heat developable photographic elements in which the benzopinacol-dye layers of the invention can be useful are described, for example, in U.S. Pat. Nos. 3,220,846; 3,301,678; 3,152,904; 3,457,075; 3,392,020; 3,669,670; and 3,801,321. Elements of this type are also described in British Pat. Nos. 1,161,777; 1,131,108; and 930,572; copending U.S. application Ser. No. 551,182 of Dickerson et al, filed Feb. 19, 1975; in *Research Disclosure*, Volume 140, Dec. 1975, Item 14049, published by Industrial Opportunities Ltd., Homewell, Havant Hampshire, P09 1EF, UK; and in copending U.S. application Ser. No. 712,459 of Merkel and Ling, filed Aug. 6, 1976 relating to α-sulfonylacetate activator stabilizers. All of these disclosures are hereby incorporated by reference.

A silver salt developing agent, typically a silver halide developing agent, is useful in the photographic materials as described. Useful silver salt developing agents, typically silver halide developing agents, include, for example, polyhydroxybenzenes such as hydroquinone developing agents, including, for example, hydroquinone, alkyl-substituted hydroquinones, such as tertiary-butylhydroquinone, methylhydroquinone, 2,5-dimethylhydroquinone and 2,6-dimethylhydroquinone; catechols and pyrogallol; chlorohydroquinone or dichlorohydroquinone; alkoxy-substituted hydroquinones such as methoxyhydroquinone or ethoxyhydroquinone; methylhydroxynaphthalene; methyl gallate; aminophenol developing agents, such as 2,4-diaminophenols and methylaminophenols; ascorbic acid developing agents such as ascorbic acid, ascorbic acid ketals and ascorbic acid derivatives; hydroxylamine developing agents such as N,N-di(2-ethoxyethyl) hydroxylamine; pyrimidine developing agents; 3-pyrazolidone developing agents such as 1-phenyl-3-pyrazolidone and 4-methyl-4-hydroxymethyl-1-phenyl-3-pyrazolidone (referred to herein as R-1), such as described in British Pat. No. 930,572 published July 3, 1963; hydroxytetronic acid and hydroxytetronimide developing agents; reductone developing agents, such as anhydrodihydropiperidino hexose reductone; and furanone developing agents such as 3,4-dihydroxy-5-phenyl-2,5-dihydro-2-furanone; and the like. Combinations of developing agents can be useful if desired.

The term "silver salt developing agent" as used herein is intended to also include developing agent precursors, that is, the term includes compounds, known as precursors, which form a developing agent, such as upon exposure to suitable energy, for example, light or heat.

A range of concentration of photographic silver salt developing agent can be useful in the described materials according to the invention. Typically, a concentration of photographic silver salt developing agent is used that is within the range of about 0.1 to about 2.0 moles of developing agent per mole of silver in the photographic material, preferably a concentration of developing agent that is within the range of 0.5 to 1.0 moles of developing agent per mole of silver in the photographic material. The optimum concentration of developing agent will depend upon a variety of factors including the particular photographic material, the particular photographic silver salt, the desired image, processing conditions and the like.

In a photographic material, as described, a useful concentration of activator precursor is typically within the range of about 0.2 to 4.0 moles of activator precursor per mole of total silver in the photographic material, preferably within the range of 0.5 to 2.0 moles of activator precursor per mole of total silver in the photographic material. The described developing agent is typically present in a concentration within the range of about 0.1 to 2.0 moles of developing agent per mole of silver, preferably within the range of about 0.5 to 1.0 moles of developing agent per mole of silver in the photographic material. The photographic silver salt, preferably photographic silver halide, is typically present in a concentration within the range of about 0.02 to about 0.3 millimoles per square decimeter of support of an element as described, preferably within the range of about 0.05 to 0.2 millimoles of photosensitive silver salt per square decimeter of support, as described. The optimum concentration of each of these components can be balanced depending upon the described factors, such as desired image, processing conditions, particular components of the photographic material and the like.

The photographic materials, as described, can also contain hardeners, antistatic layers, plasticizers, lubricants, coating aids, matting agents, brighteners, and absorbing and filter dyes which do not adversely affect the properties of the heat developable materials of the invention. These addenda are described, for example, in the *Product Licensing Index*, Volume 92, Dec. 1971, publication 9232, published by Industrial Opportunities Ltd., Homewell, Havant Hampshire, PO9 1EF, UK.

The photographic materials of the invention can contain spectral sensitizing dyes to confer additional sensitivity to the light-sensitive silver salts, especially light-sensitive silver halide as described. Useful spectral sensitizing dyes are described, for example, in the above *Product Licensing Index* publication. Combinations of spectral sensitizing dyes can be useful if desired. In addition, supersensitizing addenda which do not absorb visible light can be useful in the described materials.

After exposure of a photographic material according to the invention to provide a developable image in the photographic material, the resulting image can be developed and, if desired, stabilized by merely heating the element to a temperature within the range of about 120° C to about 200° C, usually within the range of about 150° C to about 180° C, until the desired image is developed. In the case of a photographic material containing the described activator-stabilizer precursor, the element can be heated until the desired image is developed and stabilized. An image is typically developed by heating the described material to the described temperature for about 1 to about 60 seconds, such as about 1 to about 30 seconds. By increasing or decreasing the time of heating, a higher or lower temperature within the described range is useful.

A variety of imagewise exposure means and energy sources can be useful for providing a latent image in the described photographic material before heating. The exposure means can be, for example, a light source, a laser, an electron beam, X-rays and the like.

Processing is typically carried out under ambient conditions of pressure and humidity. Pressures and humidity outside normal atmospheric conditions can be useful, if desired; however, normal atmospheric conditions are preferred.

A variety of means is useful for providing the necessary heating, as described. The photographic elements, according to the invention, can be brought into contact with a simple hot plate, heated iron, rollers, dielectric heating means, hot air heating means, microwave heating means or the like.

The following examples are included for a further understanding of the invention.

EXAMPLES 1–32

Coating compositions were prepared containing 0.75 g of polysulfonamide binder, 0.03 g p-toluenesulfonic acid, 0.1 g of benzopinacol described hereafter, about 6 ml of a solvent containing 1:1 by volume acetone and 2-methoxyethanol and either 0.05 mole of Sudan Black B dye per mole of benzopinacol or 0.1 mole of N,N-dimethyl-p-(4-nitrophenylazo)aniline per mole of benzopinacol. Coatings were made from these coating compositions on poly(ethylene terephthalate) support at a wet laydown of 0.10 mm and dried at 24° C. The polysulfonamide binder has recurring units of the structure:

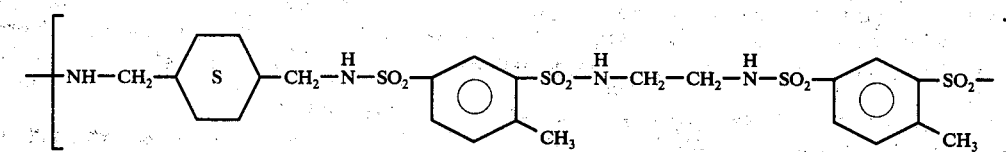

Sudan Black B azo dye has the structural formula:

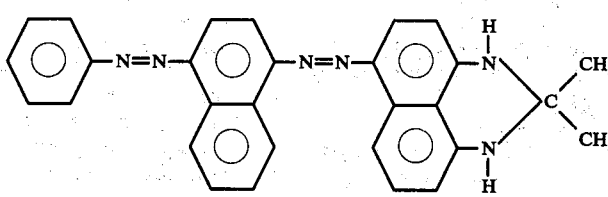

The coatings were thermally bleached by contacting the back of the coating to a heated aluminum block. The data in the Table show the benzopinacol used and the temperatures and times required to bleach the dye to a constant D-min. Unless otherwise indicated, the data is for fresh coatings.

TABLE

| Example | Benzopinacol | Dye* | °C | Temp. (sec) | Time | Comments |
|---|---|---|---|---|---|---|
| 1 | 4,4''-dimethoxy-2,3,5,6,2''',3''',5''',6'''-octafluorobenzopinacol | A | 150 | 1 | | (after preparation) |
| | | A | 150 | 1-2 | | (after storage for 7 months) |
| 2 | 4,4''-di(4-methoxyphenoxy)-2,3,5,6,2''',3''',5''',6'''-octafluorobenzopinacol | A | 150 | 1 | | |
| 3 | 4,4''-di(4-methylphenoxy)-2,3,5,6,2''',3''',5''',6'''-octafluorobenzopinacol | A | 150 | 1 | | |
| 4 | 4,4''-diphenoxy-2,3,5,6,2''',3''',5''',6'''-octafluorobenzopinacol | A | 150 | 1 | | |
| 5 | 4,4',4''',4''''-tetramethoxy-2,3,5,6,2',2''',3''',5''',6''',2''''-decafluorobenzopinacol | A | 140 | 1-2 | | (after preparation) |
| | | A | 150 | 0.5-1 | | (after storage for 7 months) |
| 6 | 4,4''-dimethyl-2',3',4',5',6',2''',3''',4''',5''',6'''-decafluorobenzopinacol | A | 150 | 1-2 | | |
| | | A | 150 | 2 | | (after storage for 15 months) |
| 7 | 2,3,5,6,2''',3''',5''',6'''-octafluorobenzopinacol | A | 160 | 2 | | |
| | | B | 160 | 2 | | |
| 8 | 2,3,4,5,6,4',2''',3''',4''',5''',6''',4''''-dodecafluorobenzopinacol | A | 160 | 1-2 | | |
| 9 | 2,3,4,5,6,2''',3''',4''',5''',6'''-decafluorobenzopinacol | A | 160 | 1-2 | | |
| | | A | 150 | 3-5 | | |
| | | A | 150 | 5 | | (after 18 months storage) |
| 10 | 4,4'''-dimethoxy-2',4',2''',4'''-tetrachloro-2,2''-difluorobenzopinacol | A | 160 | 40 | | |
| 11 | 4',4'''-dicyclohexyl-2,3,4,5,6,2''',3''',4''',5''',6'''-decafluorobenzopinacol | A | 150 | 1 | | |
| | | A | 110 | 45 | | |
| 12 | 4,4''-dichloro-2',3',4',5',6',2''',3''',4''',5''',6'''-decafluorobenzopinacol | B | 160 | 1-2 | | |
| | | B | 140 | 2-3 | | |
| | | B | 130 | 6 | | |
| | | B | 123 | 12 | | |
| | | B | 150 | 3 | | (after storage for 13 months) |
| 13 | 1,2-di-β-(5,6,7,8-tetrahydronaphthyl)-1,2-di(2,3,4,5,6-pentafluorophenyl)ethanediol | A | 150 | 3 | | |
| 14 | 2,4,2'',4''-tetrachloro-2',3',4',5',6',2''',3''',4''',5''',6'''-decafluorobenzopinacol | A | 150 | 3 | | |
| 15 | 4,4''-di(tertiarybutyl)-2',3',4',5',6',2''',3''',4''',5''',6'''-decafluorobenzopinacol | A | 160 | 1-2 | | |
| 16 | 4,4''-dihydro-octadecafluorobenzopinacol | A | 160 | 1-2 | | (film not stable in storage, after 11 days, OD = .15 after thermal exposure at 160° C) |
| 17 | 4,4''-dihydroxy-2,3,5,6,2''',3''',5''',6'''-octafluorobenzopinacol | A | 160 | 1-2 | | |
| 18 | 1,2-dimethyl-1,2-di(2,3,4,5,6-pentafluorophenyl)ethanediol (comparative example) | A | 200 | 20 | | (only partially bleached, at longer thermal exposure, film disintegrates) |
| 19 | 4,4''-dibromo-2',4',2''',4'''-tetrachlorobenzopinacol | A | 160 | 20 | | |
| 20 | 2,4,2',3',4',5',6',2''',4''',2''''',5''''',6'''''-tetradecafluorobenzopinacol | A | 160 | 1-2 | | |
| 21 | 4,4''-di(trifluoromethyl)benzopinacol | B | 160 | 20 | | |
| | | B | 180 | 15 | | (after storage for 15 months) |
| 22 | 2,4,2'',4''-tetrafluoro-2',4',2''',4'''-tetrachlorobenzopinacol | A | 160 | 20 | | |
| | | A | 180 | 5 | | (after storage for 20 months) |
| 23 | 2,3',2'',3'''-tetrafluorobenzopinacol | B | 160 | 30 | | |
| | | B | 180 | 10 | | (after storage for 14 months) |
| 24 | 3,3',3'',3'''-tetrafluorobenzopinacol | B | 160 | 30 | | |
| 25 | 3,4,2',4',3'',4'',2''',4'''-octachlorobenzopinacol | B | 190 | 2 | | |
| 26 | 2,4,2'',4''-tetrafluorobenzopinacol | B | 190 | 3 | | |
| 27 | 2,2''-dichloro-3,3''-di(trifluoromethyl)benzopinacol | B | 190 | 3 | | |
| 28 | unsubstituted benzopinacol | A | 200 | 20 | | |
| 29 | 4,4',4'',4'''-tetrafluorobenzopinacol | A | 180 | 30 | | |
| 30 | 4,4',4'',4'''-tetrachlorobenzopinacol | A | 170 | 30 | | |
| 31 | 4,2',4'',4''',2'''',4''''-hexachlorobenzopinacol | A | 160 | 20 | | |
| 32 | Eicosafluorobenzopinacol | A | 160 | 1-2 | | (film unstable in storage, after 5 days OD = .233 after thermal exposure at 160°) |

*Dyes:
A = N,N-Dimethyl-p-(nitrophenylazo)aniline
B = Sudan Black B

EXAMPLE 33

A coating composition was prepared by dissolving 2.0 mg of N,N-dimethyl-p-(nitrophenylazo)aniline, 15.0 mg of toluenesulfonic acid, and 50 mg of 2,3,4,5,6,2″,3″,4″,5″,6″-decafluorobenzopinacol in 1.0 ml of 2-butanone, and adding the solution to 2.0 ml of a 20 percent solution of a polysulfonamide dissolved in 1:1 by volume acetone: 2-methoxyethanol. The mixture was coated on poly(ethylene terephthalate) film support using a doctor blade. The element was dried at 46° C on the coating block for 15 minutes. A strip of the film was bleached by heating at 150° C for 2–3 seconds. The film was bleached from an initial visual density of 1.20 at λ = 515 nm to a density of 0.03 after the heat treatment. The density of the heat developed film was <0.1 throughout the visible region (400–800 nm). The heat sensitivity of another sample of this film after four months of storage at room temperature was the same as that of the initial film.

EXAMPLE 34

A film sample was made for use as an antihalation layer for thermally developable photographic film. The film was made using three dyes, yellow, red, and blue: the yellow dye is 3,5,3′,5′-tetramethylbis-2,5-cyclohexadiene-1-ylidene-4,4′-dione, the red dye is N,N-dimethyl-4-(4-nitrophenylazo) aniline, and the blue dye is 3-acetamido-N,N-bis(acetoxyethyl)-4-(2-chloro-4,6-dinitrophenylazo)-6-methoxyaniline.

The dyes (5 mg of each) were dissolved with 100 mg of 2,3,4,5,6,2″,3″,4″,5″,6″-decafluorobenzopinacol in 1.0 ml of 2-butanone. The solution was mixed with 2 ml of the 20 percent polysulfonamide solution described in Example 1, coated, and dried as in Example 1. The film readily bleached when heated to 150° C. Similar results were obtained with the film held in storage for 4 months.

EXAMPLE 35

A film sample was prepared as described in Example 34, except using 5 mg of Sudan Black B in place of the yellow, red, and blue dyes, 50 mg of decafluorobenzopinacol, and 5 mg of toluenesulfonic acid. All other conditions were the same. The black dye composition bleached readily when heated at 150°–160° C, although the sample was stable at room temperature for a long period of time.

EXAMPLE 36

Three quantities of a gram of the polysulfonamide poly(ethylene-co-1,4-cyclohexylenedimethylene-1-methyl-2,4-benzenedisulfonamide) in which the ethylene and 1,4-cyclohexylenedimethylene moieties were present on a 50/50 mole percent basis was dissolved in 6.025 gm of methoxyethanol by stirring and gentle heating. A clear lacquer solution resulted. Ten milligrams of Sudan Black B along with 100 mg of 2,3,4,5,6,2′,3′,4′,5′,6′-decafluorobenzopinacol were added to the polymer solution. The dye and benzopinacol were dissolved by continued stirring at ambient temperature. The clear lacquer solution was coated at 16° C on to a poly(ethylene terephthalate) film support and dried at 29° C to remove residual solvent.

A sample of the above element measured on a McBeth densitometer had a visual density of 0.47. When the film was heated for one second at 160° C, the visual density was reduced to 0.06. The stability of the bleachable element was determined by heating a sample of the film at 58° C for prolonged periods. After storage of the element at 58° C, ambient humidity for 336 hours, the visual density was 0.43. Heating to 160° C reduced the visual density of the stored element from 0.43 to 0.07. Extrapolation of the thermal stability of the bleachable element from 58° C to ambient temperature seems to indicate a shelf life stability of greater than one year at room temperature.

EXAMPLE 37

The following materials were mixed:

| | |
|---|---|
| gelatin | 200 mg |
| surfactant (Surfactant 10G which is an alkylphenoxypolyglycidol sold by Olin Corporation, U.S.A.) | 10 mg |
| bis(2-amino-2-thiazoline)methylenebis(sulfonylacetate) | 500 mg |
| 4-methyl-4-hydroxymethyl-1-phenyl-3-pyrazolidone | 100 mg |
| silver bromoiodide gelatino emulsion (2.5 mole percent iodide, 0.1 micron reduction sensitized silver bromoiodide) | 100 mg (Ag) |
| water to make | 10 ml |

This composition is described in Example 1 of copending application U.S. Ser. No. 712,459 filed Aug. 6, 1976 entitled "Sulfonylacetate Activator Stabilizer Precursor", of Merkel and Ling.

The composition was coated at 100 microns wet thickness on a poly(ethylene terephthalate) film support and permitted to dry. The other side of the film support was coated with the benzopinacol-dye composition described in Example 36. An imagewise exposed sample of this element was processed at 160° C for 10 seconds. An image was formed on a substantially clear background. Compared to an identical coating not having the benzopinacol-dye layer, this element showed a large increase in halation protection.

EXAMPLE 38

A sample was prepared as in Example 33 using 100 mg instead of 50 mg of the benzopinacol and 7 mg instead of 2 mg of azo dye. The film was coated with a doctor blade. One portion of the sample was completely bleached by heating at 150° C for only one second. Another portion of the sample was exposed to high intensity Argon ion laser light of 515 nm. The sample bleached readily in the exposed areas using a rate of writing of the focused laser light of 10 m/sec.

EXAMPLE 39

Another sample was prepared as described for Example 38, except using only 30 mg of the benzopinacol. The film readily bleached at 150° C, but not as completely. The optical density of the film at 525 nm was 1.05 before heating and 0.24 after heating for 20 seconds. A piece of the film was stored in an oven at a temperature of 55° C for 147 hours.

The optical density of the stored film at 515 nm was 1.06 prior to heating at 150° C for 20 seconds, and 0.26 after heating. Another piece of the film was stored at room temperature for 100 days. After storage it had an optical density of 1.06 at 515 nm which was reduced to 0.28 by heating at 150° C for 20 seconds. This indicates that the optical density of the film does not change substantially with age. The extent to which it can be bleached, however, slightly decreases with age (estimated to be less than 15% per year). It is apparent that by using an excess of the benzopinacol a film can be made which will completely bleach if used within a specified interval of time after manufacturing.

EXAMPLE 40

Ethyl red (2.0 mg), 1,1'-diethyl-2,4'-cyanine iodide, (Eastman Kodak 2155) was dissolved in 2.0 ml of acetone/2-methoxyethanol. Then, 50 mg of 4,4'''-dimethoxy-2,3,5,6,2'',3'',5'',6''-octafluorobenzopinacol was added. The solution was mixed with 1.0 ml of 20 percent polysulfonamide polymer solution (acetone/2-methoxyethanol 1/1). The solution was mixed and coated at a 0.004 inch wet coating thickness on poly(ethylene terephthalate) film base, using a coating knife blade. It was allowed to dry at 49° C for 15 minutes. The dye in the film had λmax at 565 nm, and at 530 nm. The optical density was 1.8 and 0.93, respectively. The film was thermally exposed at 160° C for 10 seconds. The optical density of the exposed film was 0.20 at λ = 565 and .18 at 530 nm. The reduction in the dye density was 89% and 81%, at the two wavelengths. The same results were obtained after the film had been held in storage at room temperature for 6 months.

EXAMPLE 41

Malachite Green (Eastman Kodak CI 42000) (2 mg), a triphenylmethane dye, and 50 mg of 2,3,4,5,6,2'',3'',4'',5'',6''-decafluorobenzopinacol were dissolved separately in approximately ½ ml of 2-butanone. The solutions were added to 2 ml of 20% polysulfonamide polymer solution (acetone/2-methoxyethanol (1/1)). The solution was mixed and coated at a 0.006 inch wet coating thickness using a knife blade. It was dried at 49° C. The film was bleached when thermally exposed at 150° C. The film had λmax at 630 nm and 395 nm with the optical density being 0.95 and 0.28, respectively. The film after thermal exposure at 150° C for 6 seconds had optical density of 0.085 at 630 nm and 0.06 at 395 nm. The thermally exposed film had optical density of 0.10 at 350 nm and lower than 0.10 throughout the region 350–750 nm. The same extent of bleaching was obtained after the film was held in storage for 18 months. The bleaching of the dye is irreversible.

EXAMPLE 42

A film prepared similarly as in Example 40 but using 1,5-diphenyl-3-(p-methoxyphenyl)formazan dye and 2,3,4,5,6,2',4',2'',3'',4'',5'',6'',2''',4'''-tetradecafluorobenzopinacol was found to bleach readily when heated at 150° C.

EXAMPLE 43

A film was prepared similarly as in Example 40, but using 3,5,3',5'-tetramethyl-4,4'-biphenylquinone and 2,3,4,5,6,2', 4',2'',3'',4'',5'',6'',2''',4'''-tetradecafluorobenzopinacol. The intense yellow color of this film was bleached upon thermal exposure at 150° C for 1–2 seconds.

EXAMPLE 44

This is a comparative example. 2,3,5-Triphenyl-2H-tetrazolium chloride is not reduced by benzopinacol under acid conditions.

(a) 2,3,5-Triphenyl-2H-tetrazolium chloride (20 mg) and 75 mg of benzopinacol were dissolved in 1.0 ml of acetone/2-methoxyethanol, 1/1. This solution was added to 2.0 ml of 20% polysulfonamide polymer (acetone/2-methoxyethanol, 1/1) solution. The solution was coated on poly(ethylene terephthalate) film support and was dried at 46° C. Then, it was thermally exposed at 185° C for 30 seconds. There was only very slight change in the films transparency. The increase in opacity was less than 0.03 O.D. Thus, the salt was not reduced by the benzopinacol to the corresponding triphenylformazan dye.

(b) The same formulation as in (a) was prepared, but 20 mg of toluene sulfonic acid was added to the solution before coating. Thermal exposure of the dried film produced exactly the same results as in (a).

(c) The same formulation as in (a) was prepared, except 20 mg of triethanolamine was added to the solution before coating.

The film formed a red dye upon thermal exposure at 190° C, 185° C, 170° C, 150° C, and 140° C within a time interval of 2 seconds. At 125° C it took 5 seconds, at 110° C — 20 seconds, and at 100° C — 30 seconds to develop the deep red color. In addition, the film which was thermally unexposed was slightly pink showing poor stability at room temperature. These data indicate that the salt was reduced only under basic conditions. Slightly acidic conditions, case (a), where the inherent acidity is due only to the slight acidity of the polymer are not suitable to effect reduction of the salt. The same was true under more strongly acidic conditions, case (b).

EXAMPLE 45

This is a comparative example.

(a) An acidic film was made by using a solution of the following composition: 2 mg of an azo dye, N,N-dimethyl-p-(nitrophenylazo)aniline, 55 mg of 2,2'-diphenyl-2,2'-dimethylethanediol, 3.0 mg of toluene sulfonic acid dissolved in 1 ml of acetone were mixed with 1 ml solution containing 20% polysulfonamide polymer in 2-methoxyethanol. The solution was coated at a 0.004 inch wet coating thickness on poly(ethylene terephthalate) base film support. It was dried at 43° C for 10 minutes. The film had λmax at 526 nm. Optical density at this wavelength was 1.13. The film was exposed thermally at 150° C and 170° C for periods of 5 to 15 seconds. The film did not bleach. The optical density at 526 nm was 0.83.

A basic film was made using the above procedure except that 4.5 mg of triethanolamine was used instead of toluene sulfonic acid.

The λmax was at 500 nm, and the optical density was 0.31. The film was exposed thermally at 150° C and 170° C for periods of 5–10 seconds. It did not bleach.

This shows that the 2,2'-diphenyl-2,2'-dimethylethanediol is ineffective under either acidic or basic conditions.

(b) Coatings were made as in (a) except decafluorobenzopinacol is used instead of 2,2'-diphenyl2,2'-dimethylethanediol. An acidic film was made by using 3 mg of toluene sulfonic acid. The film had λmax at 522 nm. It readily bleached when exposed at 150° C for a period of 2–5 seconds.

A basic film was made using 4.0 mg of triethanolamine in the coating composition. The film had λmax at 492 nm. After exposure at 150° for 2–5 seconds, only 77.3% density reduction was obtained. After 2 days in storage the film was again exposed at 150° for 2–5 seconds. Only 11.4% reduction in density was obtained indicating that the film under basic conditions is not stable.

The invention has been described in detail with particular reference to certain preferred embodiments thereof, but it will be understood that variations and modifications can be effected within the spirit and scope of the invention. What is claimed is:

1. An imaging element comprising a support having thereon a neutral or acidic heat bleachable layer comprising (i) a binder, (ii) a benzopinacol which forms ketyl radicals on heating to a temperature above 100° C and (iii) a reducible dye or a reducible dye precursor that can react with said ketyl radicals.

2. An imaging element according to claim 1 wherein said benzopinacol is represented by the formula:

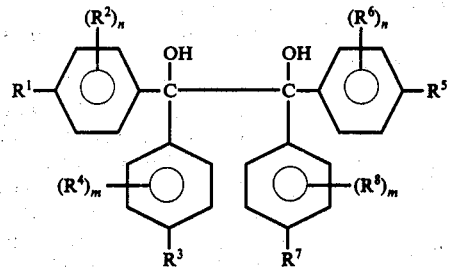

wherein each $R^1$ and $R^5$ is independently selected from halogen atoms, alkyl of about 1 to 10 carbon atoms, alkoxy having about 1 to 10 carbon atoms, phenoxy having about 6 to 12 carbon atoms and hydroxy; $R^3$ and $R^7$ are independently selected from hydrogen atoms or any of the groups specified for $R^1$ and $R^5$; each $R^2$, $R^4$, $R^6$, and $R^8$ is independently selected from halogen atoms and from trifluoromethyl with the proviso that both ortho positions on each of the four phenyl groups can be substituted only when both substituents are fluorine; each $n$ independently is an integer of from 1 to 4; and each $m$ independently is an integer of from 0 to 4.

3. An imaging element according to claim 1 wherein said benzopinacol is represented by the formula:

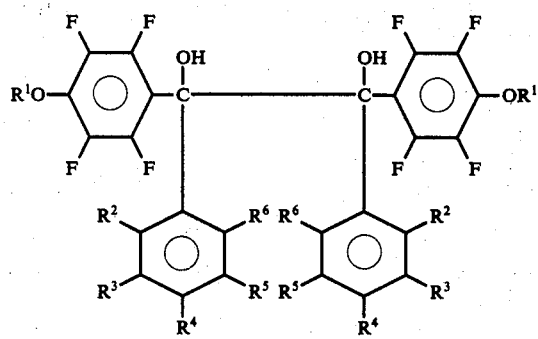

wherein:
$R^1$ is hydrogen, alkyl or aryl;
$R^2$ and $R^6$ independently are selected from the group consisting of hydrogen, halogen or trifluoromethyl;
$R^3$ and $R^5$ independently are selected from the group consisting of hydrogen, halogen and alkyl or, when taken together with $R^4$, represent a tetramethylene group; and
$R^4$ is selected from the group consisting of hydrogen, halogen, alkyl, alkoxy and phenoxy;

with the proviso that when both of the ortho positions of the phenyl groups at which $R^2$ and $R^6$ are attached are substituted, the substituent is fluorine.

4. An imaging element according to claim 1 wherein said benzopinacol forms ketyl radicals on heating to a temperature of 160° C for less than 10 seconds.

5. An imaging element according to claim 1 wherein said benzopinacol is 4,4''-dimethoxy-2,3,5,6,2'',3'',5'',6''-octafluorobenzopinacol.

6. An imaging element according to claim 1 wherein said binder is a polysulfonamide binder which has in the backbone of or pendent therefrom the moiety —$SO_2$—N< and has a wavelength of maximum absorption no greater than about 350 nm in the spectral range from 200 to 750 nm.

7. An imaging element according to claim 1 wherein said binder is a polysulfonamide binder containing toluene-2,4-disulfonamide or N-(vinylphenyl) sulfonamide units and has a wavelength of maximum absorption no greater than about 350 nm in the spectral range from 200 to 750 nm.

8. An imaging element according to claim 1 wherein said binder is poly(ethylene-co-1,4-cyclohexylenedimethylene-1-methyl-2,4-benzenedisulfonamide).

9. An imaging element according to claim 1 wherein said dye is an azo dye.

10. An imaging element according to claim 1 wherein said dye is N-benzyl-N-ethyl-3-acetamido-4-(2-cyano-4,6-dinitrophenylazo)aniline.

11. An imaging element according to claim 1 wherein said dye is present in a concentration sufficient to provide an optical density of at least 0.05 in the visible region, 400–750 nm, and said benzopinacol is present in a concentration sufficient to reduce the density of said dye by at least 10% when said element is heated above 100° C.

12. A photographic element comprising a support having thereon (a) a neutral or acidic heat bleachable layer comprising (i) a binder, (ii) a benzopinacol which forms ketyl radicals on heating to a temperature above 100° C and (iii) a reducible dye or a reducible dye precursor that can react with said ketyl radicals and (b) a photosensitive layer, comprising a photographic silver salt, a photographic silver salt developing agent, a binder and a heat-activatable activator for the aforesaid developing agent.

13. A photographic element according to claim 12 wherein said benzopinacol is represented by the formula:

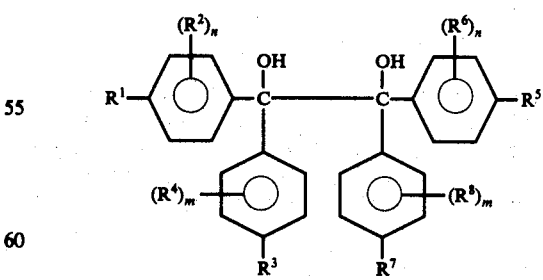

wherein each $R^1$ and $R^5$ is independently selected from halogen atoms, alkyl of about 1 to 10 carbon atoms, alkoxy having about 1 to 10 carbon atoms, phenoxy having about 6 to 12 carbon atoms and hydroxy; $R^3$ and $R^7$ are independently selected from hydrogen atoms or any of the groups specified for $R^1$ and $R^5$; each $R^2$, $R^4$, $R^6$, and $R^8$ is independently selected from halogen atoms and from trifluoromethyl with the proviso that both ortho positions on each of the four phenyl groups can be substituted only when both substituents are fluorine; each $n$ independently is an integer of from 1 to 4; and each $m$ independently is an integer of from 0 to 4.

14. A photographic element according to claim 12 wherein said benzopinacol is represented by the formula:

[Chemical structure showing a benzopinacol with two central carbons each bearing OH groups and four substituted phenyl rings. The upper two phenyl groups carry F substituents at multiple positions and OR¹ groups. The lower two phenyl groups carry R², R³, R⁴, R⁵, R⁶ substituents.]

wherein:
$R^1$ is hydrogen, alkyl or aryl;
$R^2$ and $R^6$ independently are selected from the group consisting of hydrogen, halogen or trifluoromethyl;
$R^3$ and $R^5$ independently are selected from the group consisting of hydrogen, halogen and alkyl or, when taken together with $R^4$, represent a tetramethylene group; and
$R^4$ is selected from the group consisting of hydrogen, halogen, alkyl, alkoxy and phenoxy;
with the proviso that when both of the ortho positions of the phenyl groups at which $R^2$ and $R^6$ are attached are substituted, the substituent is fluorine.

15. A photographic element according to claim 12 wherein said benzopinacol forms ketyl radicals on heating to a temperature of 160° C for less than 10 seconds.

16. A photographic element according to claim 12 wherein said benzopinacol is 4,4'''-dimethoxy-2,3,5,6,2''',3''',5''',6'''-octafluorobenzopinacol.

17. A photographic element according to claim 12 wherein said binder is a polysulfonamide binder which has in the backbone of or pendent therefrom the moiety $-SO_2-N<$ and has a wavelength of maximum absorption no greater than about 350 nm in the spectral range from 200 to 750 nm.

18. A photographic element according to claim 12 wherein said binder is a polysulfonamide binder containing toluene-2,4-disulfonamide or N-(vinylphenyl)sulfonamide units and has a wavelength of maximum absorption no greater than about 350 nm in the spectral range from 200 to 750 nm.

19. A photographic element according to claim 12 wherein said binder is poly(ethylene-co-1,4-cyclohexylenedimethylene-1-methyl-2,4-benzenedisulfonamide).

20. A photographic element according to claim 12 wherein said dye is an azo dye.

21. A photographic element according to claim 12 wherein said dye is N-benzyl-N-ethyl-3-acetamido-4-(2-cyano-4,6-dinitrophenylazo)aniline.

22. A photographic element according to claim 12 wherein said dye is an azo dye and is present in a concentration sufficient to produce an optical density of at least 0.3 and the molar ratio of said benzopinacol to said dye is between about 1:1 and 4:1.

23. A photothermographic element comprising a support having thereon (1) a neutral or acidic heat bleachable antihalation layer comprising (i) a binder, (ii) a benzopinacol represented by the formula:

[Chemical structure showing a benzopinacol with two central carbons each bearing OH groups and four substituted phenyl rings bearing $(R^2)_n$, $(R^6)_n$, $(R^4)_m$, $(R^8)_m$, and $R^1$, $R^3$, $R^5$, $R^7$ substituents.]

wherein each $R^1$ and $R^5$ is independently selected from halogen atoms, alkyl of about 1 to 10 carbon atoms, alkoxy having about 1 to 10 carbon atoms, phenoxy having about 6 to 12 carbon atoms and hydroxy; $R^3$ and $R^7$ are independently selected from hydrogen atoms or any of the groups specified for $R^1$ and $R^5$; each $R^2$, $R^4$, $R^6$, and $R^8$ is independently selected from halogen atoms and from trifluoromethyl with the proviso that both ortho positions on each of the four phenyl groups can be substituted only when both substituents are fluorine; each $n$ independently is an integer of from 1 to 4; and each $m$ independently is an integer of from 0 to 4; a polysulfonamide binder which has in the backbone or pendent therefrom the moiety $-SO_2-N<$ and has the wavelength of maximum absorption no greater than about 350 nm in the spectral range from 200 to 750 nm and (iii) an azo dye; and (2) a heat developable and heat stabilizable photosensitive layer comprising (a) a photographic silver salt, (b) a photographic silver salt developing agent, (c) a binder and (d) a heat activatable activator-stabilizer.

24. A photothermographic element comprising a support having thereon (1) a neutral or acidic heat bleachable antihalation layer comprising (i) a binder, (ii) a benzopinacol represented by the formula:

[Chemical structure showing a benzopinacol with two central carbons each bearing OH groups. The upper two phenyl groups bear F substituents and OR¹ groups. The lower two phenyl groups bear R², R³, R⁴, R⁵, R⁶ substituents.]

wherein:
$R^1$ is hydrogen, alkyl or aryl;
$R^2$ and $R^6$ independently are selected from the group consisting of hydrogen, halogen or trifluoromethyl;
$R^3$ and $R^5$ independently are selected from the group consisting of hydrogen, halogen and alkyl or, when taken together with $R^4$, represent a tetramethylene group; and R⁴ is selected from the group consisting of hydrogen, halogen, alkyl, alkoxy and phenoxy;

with the proviso that when both of the ortho positions of the phenyl groups at which $R^2$ and $R^6$ are attached are substituted, the substituent is fluorine; a polysulfonamide binder which has in the backbone or pendent therefrom the moiety —SO$_2$—N< and has the wavelength of maximum absorption no greater than about 350 nm in the spectral range from 200 to 750 nm and (iii) an azo dye; and (2) a heat developable and heat stabilizable photosensitive layer comprising (a) a photographic silver salt, (b) a photographic silver salt developing agent, (c) a binder and (d) a heat activatable activator-stabilizer.

25. The photothermographic element of claim 24 wherein said benzopinacol is 4,4″-dimethoxy-2,3,5,6,2″,3″,5″,6″-octafluorobenzopinacol; and said binder is a polysulfonamide containing toluene-2,4-disulfonamide or N-(vinylphenyl) sulfonamide units.

26. A photothermographic element comprising a support having thereon (1) a neutral or acidic heat bleachable antihalation layer comprising (i) a polysulfonamide binder containing toluene-2,4-disulfonamide or N-(vinylphenyl) sulfonamide units, (ii) 4,4″-dimethoxy-2,3,5,6,2″,3″,5″,6″-octafluorobenzopinacol and (iii) an azo dye consisting essentially of N-benzyl-N-ethyl-3-acetamido-4-(2-cyano-4,6-dinitrophenylazo)aniline and (2) a heat developable and heat stabilizable photosensitive layer comprising (a) a gelatino photographic silver halide emulson, (b) a photographic silver halide developing agent, (c) a polymeric binder and (d) a heat activatable activator-stabilizer.

27. A method of processing an imagewise exposed, photothermographic element comprising a support having thereon (1) a neutral or acidic heat bleachable, colored layer comprising (i) a binder, (ii) a benzopinacol which forms ketyl radicals on heating to a temperature above 100° C and (iii) a reducible dye or a reducible dye precursor that can react with said ketyl radicals, and (2) a photosensitive layer comprising (a) a photographic silver salt, (b) a photographic silver halide developing agent, (c) a binder, and (d) a heat activatable activator for said developing agent, comprising heating said element to a temperature within the range of about 110° C to about 200° C until an image is developed in said photosensitive layer and until at least 90% of said colored layer is changed to colorless.

28. A method of processing an imagewise exposed, photothermographic element comprising a support having thereon (1) a neutral or acidic heat bleachable antihalation layer comprising (i) a polysulfonamide binder containing toluene-2,4-disulfonamide or N-(vinylphenyl) sulfonamide units, (ii) 4,4″-dimethoxy-2,3,5,6,2″,3″,5″,6″-octafluorobenzopinacol and (iii) an azo dye consisting essentially of N-benzyl-N-ethyl-3-acetamido-4-(2-cyano-4,6-dinitrophenylazo)aniline and (2) a heat developable and heat stabilizable photosensitive layer comprising (a) a gelatino photographic silver halide emulsion, (b) a photographic silver halide developing agent, (c) a polymeric binder and (d) a heat activatable activator-stabilizer; comprising heating said element to a temperature within the range of about 110° C to about 200° C until an image is developed and stabilized in said photosensitive layer and until at least 90% of said colored layer is changed to colorless.

* * * * *

UNITED STATES PATENT AND TRADEMARK OFFICE
CERTIFICATE OF CORRECTION

PATENT NO. : 4,081,278
DATED : March 28, 1978
INVENTOR(S) : Jonas Dedinas and George L. Fletcher, Jr.

It is certified that error appears in the above-identified patent and that said Letters Patent are hereby corrected as shown below:

Column 1, line 43, "Sorenson" should read ---Sorensen---.

Columns 13 and 14, under Table, the heading "Dye*" should be moved directly above the column beginning with "A".

Columns 13 and 14, under Table, the heading "Temp. °C" should be placed directly above the column beginning with "150".

Columns 13 and 14, under Table, the heading "Time (sec)" should be placed directly above the column beginning with "1".

Columns 13 and 14, under Table, the heading "Comments" should be placed directly above the column beginning with "(after preparation)".

Column 13, Example 20, should read ---2,4,2',3',4',5',6', 2",4",2"',4"',5"',6"'-tetradecafluorobenzopinacol---.

Column 15, line 26, "the" should read ---The---.

Column 18, line 57, "2,2'-diphenyl2,2'-" should read --- 2,2'-diphenyl-2,2'- ---.

Signed and Sealed this

Nineteenth Day of September 1978

[SEAL]

Attest:

RUTH C. MASON
Attesting Officer

DONALD W. BANNER
Commissioner of Patents and Trademarks